US011957489B2

(12) United States Patent
Androulakis

(10) Patent No.: US 11,957,489 B2
(45) Date of Patent: Apr. 16, 2024

(54) TEMPERATURE CONTROL OF AN ENVIRONMENT TO ACHIEVE OCCUPANT COMFORT BASED ON HEART RATE VARIABILITY PARAMETERS

(71) Applicant: GENTHERM INC., Northville, MI (US)

(72) Inventor: Ioannis Androulakis, Livonia, MI (US)

(73) Assignee: Gentherm Inc., Northville, MI (US)

( * ) Notice: Subject to any disclaimer, the term of this patent is extended or adjusted under 35 U.S.C. 154(b) by 884 days.

(21) Appl. No.: 16/962,738

(22) PCT Filed: Jan. 23, 2019

(86) PCT No.: PCT/US2019/014769
§ 371 (c)(1),
(2) Date: Jul. 16, 2020

(87) PCT Pub. No.: WO2019/147684
PCT Pub. Date: Aug. 1, 2019

(65) Prior Publication Data
US 2020/0352514 A1   Nov. 12, 2020

Related U.S. Application Data

(60) Provisional application No. 62/621,315, filed on Jan. 24, 2018.

(51) Int. Cl.
*A61B 5/00* (2006.01)
*A61B 5/024* (2006.01)
(Continued)

(52) U.S. Cl.
CPC .......... *A61B 5/6893* (2013.01); *A61B 5/0006* (2013.01); *A61B 5/0008* (2013.01);
(Continued)

(58) Field of Classification Search
CPC . F24F 2110/30; F24F 2120/14; F24F 2130/20
See application file for complete search history.

(56) References Cited

U.S. PATENT DOCUMENTS

2003/0093002 A1   5/2003   Kuo
2016/0061472 A1   3/2016   Lee et al.
(Continued)

FOREIGN PATENT DOCUMENTS

EP    0615197 A1        9/1994
WO   WO-2014014862 A2  1/2014

OTHER PUBLICATIONS

International Search Report and Written Opinion of the ISA issued in PCT/US2019/014769, dated Apr. 17, 2019; ISA/EP.
(Continued)

*Primary Examiner* — Joseph F Trpisovsky

(57) ABSTRACT

A temperature control system includes a heating, ventilation and air conditioning (HVAC) system configured to control temperature in an environment. A sensor is configured to generate an electrocardiogram (ECG) signal for an occupant of the environment. An environmental sensor is configured to sense environmental data selected from a group consisting of temperature, air velocity, sun load and humidity. A heart rate variability (HRV) controller is configured to receive the ECG signal; identify inter-beat intervals based on the ECG signal; and control the HVAC system based on the inter-beat intervals and the environmental data.

22 Claims, 13 Drawing Sheets

(51) Int. Cl.
  *B60H 1/00* (2006.01)
  *F24F 11/58* (2018.01)
  *F24F 11/64* (2018.01)
  *F24F 11/65* (2018.01)
  *F24F 110/10* (2018.01)
  *F24F 110/20* (2018.01)
  *F24F 110/30* (2018.01)
  *F24F 120/14* (2018.01)
  *F24F 130/20* (2018.01)

(52) U.S. Cl.
  CPC ........ *A61B 5/0022* (2013.01); *A61B 5/02405* (2013.01); *A61B 5/7264* (2013.01); *B60H 1/00742* (2013.01); *F24F 11/58* (2018.01); *F24F 11/64* (2018.01); *F24F 11/65* (2018.01); *F24F 2110/10* (2018.01); *F24F 2110/20* (2018.01); *F24F 2110/30* (2018.01); *F24F 2120/14* (2018.01); *F24F 2130/20* (2018.01)

(56) References Cited

U.S. PATENT DOCUMENTS

2016/0354027 A1* 12/2016 Benson ................ A61B 5/0533
2017/0321921 A1* 11/2017 Chen .................... H04M 19/04
2018/0231269 A1* 8/2018 Hiei ...................... G16H 40/63

OTHER PUBLICATIONS

Nkurikiyeyezu, Kizito N. et al. "Heart Rate Variability as a Predictive Biomarker of Thermal Comfort". Wearable Information Lab. Aoyama Gakuin University. 4 Chome 4-25 Shibuya, Shibuya City, Tokyo 150-8366. http://www.wil.it.aoyama.ac.jp/. Feb. 21, 2017; 16 pages.

Office Action dated Jun. 20, 2023 from Japanese Patent Office for Japanese Patent Application No. 2020-538954 (with English Translation).

* cited by examiner

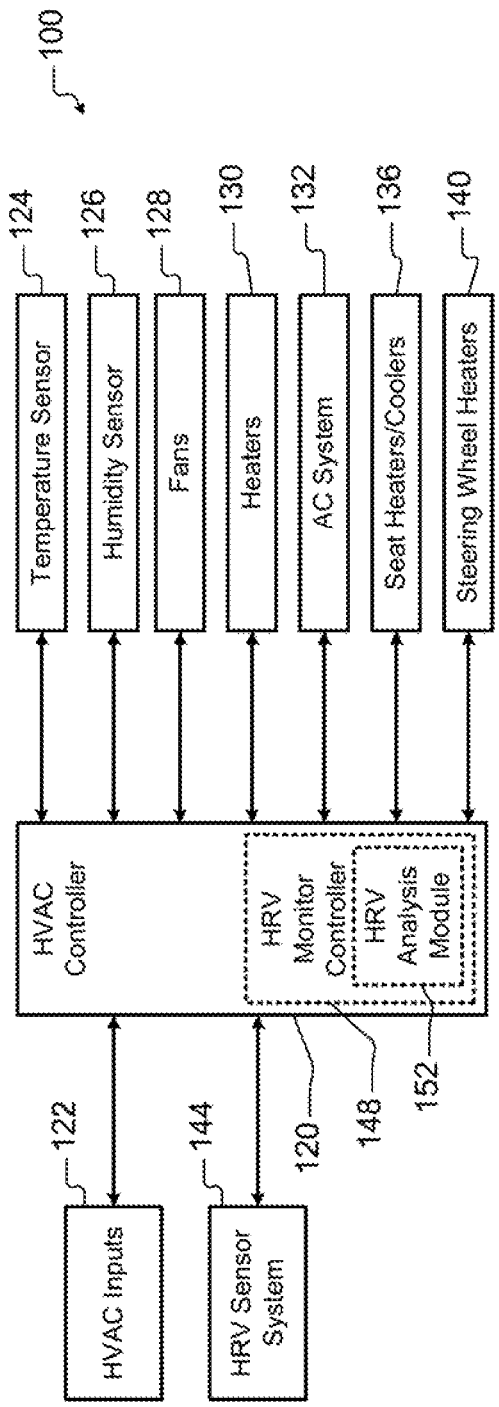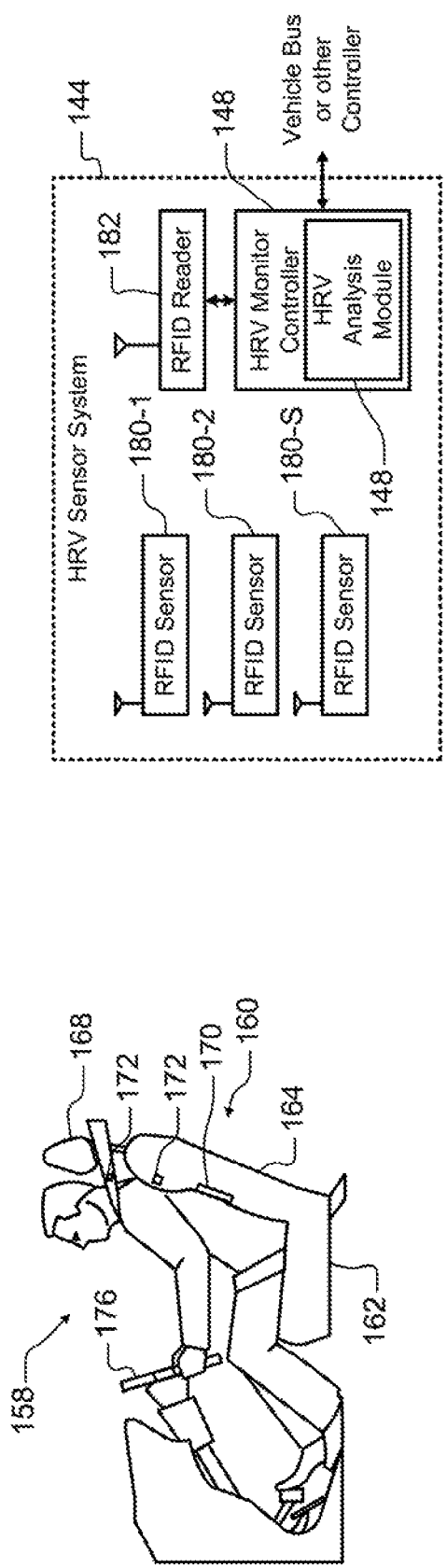

TEMPERATURE CONTROL OF AN ENVIRONMENT TO ACHIEVE OCCUPANT COMFORT BASED ON HEART RATE VARIABILITY PARAMETERS

CROSS-REFERENCE TO RELATED APPLICATIONS

This application is a U.S. National Phase Application under 35 U.S.C. 371 of International Application No. PCT/US2019/014769, filed on Jan. 23, 2019, which claims the benefit of U.S. Provisional Patent Application Ser. No. 62/621,315, filed on Jan. 24, 2018. The entire disclosures of the above applications are; hereby incorporated by reference in their entirety.

FIELD

The present disclosure relates to systems and methods for controlling temperature in an environment to increase occupant comfort based at least in part on one or more heart rate variability (HRV) parameters.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Heating, ventilation and air-conditioning (HVAC) systems are used to provide temperature control in environments such as vehicles, buildings and/or other spaces. Conditions such as temperature and/or humidity within an environment impact whether or not an occupant is comfortable with respect to temperature. The occupants in the environment can set a temperature set point to attempt to achieve occupant comfort. However, for a given temperature set point, different occupants may have different levels of thermal comfort. Thermal comfort is defined as a condition of the mind that expresses a level of satisfaction or dissatisfaction with a particular thermal environment.

SUMMARY

A temperature control system includes a heating, ventilation and air conditioning (HVAC) system configured to control temperature in an environment. A sensor is configured to generate an electrocardiogram (ECG) signal for an occupant of the environment. An environmental sensor is configured to sense environmental data selected from a group consisting of temperature, air velocity, sun load and humidity. A heart rate variability (HRV) controller is configured to receive the ECG signal; identify inter-beat intervals based on the ECG signal; and control the HVAC system based on the inter-beat intervals and the environmental data.

In other features, the environment comprises a vehicle interior and the HVAC system includes a fan, a heater and an air conditioner. The temperature control system includes at least one of a seat heater, a seat heater/cooler and a steering wheel heater. The HRV controller controls the at least one of the seat heater, the seat heater/cooler and the steering wheel heater based on the inter-beat intervals.

In other features, the HRV controller is further configured to compare the inter-beat intervals to a first threshold and a second threshold, wherein the first threshold is greater than the second threshold; increase heating in the environment when at least one of the inter-beat intervals is less than the first threshold; and increase cooling in the environment when at least one of the inter-beat intervals is greater than the second threshold.

In other features, the HRV controller is further configured to adjust at least one of the first threshold and the second threshold in response to a manual setpoint change to the HVAC system; and use the at least one of the adjusted first threshold and the adjusted second threshold to control the HVAC system.

In other features, the HRV controller is further configured to compare variations in the inter-beat intervals to a predetermined variation threshold; control the HVAC system using a temperature setpoint when the variations are greater than the predetermined variation threshold; and control the HVAC system using a correlation between the inter-beat intervals and comfort of the occupant of the environment when the variations are less than the predetermined variation threshold.

In other features, the HRV controller is further configured to generate N HRV parameters based on the inter-beat intervals, where N is an integer greater than one; and use a comfort classification model defined in N-dimensional HRV parameter space.

In other features, the HRV controller is further configured to determine the comfort of the occupant of the environment based on the N HRV parameters and the comfort classification model. The comfort classification model defines at least one comfort region in the N-dimensional HRV parameter space and at least one discomfort region in the N-dimensional HRV parameter space. The HRV controller is further configured to train the comfort classification model based on manual setpoint changes to the HVAC system.

A vehicle includes the temperature control system and a telematics system. The HRV controller is further configured to transmit data relating to the N HRV parameters, the environmental data and manual setpoint changes to the HVAC system via the telematics system to a remote classification training system; and receive an updated comfort classification model via the telematics system from the remote classification training system.

In other features, the HRV controller is further configured to, in response to a manual setpoint change to the HVAC system, retrain the classification model based on the manual setpoint change.

A method for controlling temperature in an environment includes controlling temperature in an environment using a heating, ventilation and air conditioning (HVAC) system; generating an electrocardiogram (ECG) signal for an occupant of the environment; generating environmental data selected from a group consisting of temperature, humidity, sun load and air velocity; identifying inter-beat intervals based on the ECG signal; and controlling the HVAC system based on the inter-beat intervals and the environmental data.

In other features, the environment comprises a vehicle interior and the HVAC system includes a fan, a heater and an air conditioner. The method includes controlling at least one of a seat heater, a seat heater/cooler and a steering wheel heater based on the inter-beat intervals.

In other features, the method includes comparing the inter-beat intervals to a first threshold and a second threshold, wherein the first threshold is greater than the second threshold; increasing heating in the environment when at least one of the inter-beat intervals is less than the first threshold; and increasing cooling in the environment when at least one of the inter-beat intervals is greater than the second threshold.

In other features, the method includes adjusting at least one of the first threshold and the second threshold in response to a manual setpoint change to the HVAC system; and using the at least one of the adjusted first threshold and the adjusted second threshold to control the HVAC system.

In other features, the method includes comparing variations in the inter-beat intervals to a predetermined variation threshold; controlling the HVAC system using a temperature setpoint when the variations are greater than the predetermined variation threshold; and controlling the HVAC system using a correlation between the inter-beat intervals and comfort of the occupant when the variation is less than the predetermined variation threshold.

In other features, the method includes generating N heart rate variability (HRV) parameters based on the inter-beat intervals, where N is an integer greater than one; and using a comfort classification model defined in N-dimensional HRV parameter space.

In other features, the method includes determining comfort of the occupant based on the N HRV parameters and the comfort classification model.

In other features, the comfort classification model defines at least one comfort region in the N-dimensional HRV parameter space and at least one discomfort region in the N-dimensional HRV parameter space.

In other features, the method includes training the comfort classification model in response to manual setpoint changes to the HVAC system. The method includes transmitting data relating to the N HRV parameters, environmental data, and manual setpoint changes to the HVAC system via a telematics system to a remote classification training system; and receiving an updated comfort classification model via the telematics system from the remote classification training system.

In other features, the method includes, in response to manual setpoint changes to the HVAC system, retraining the classification model.

A method for controlling temperature in an environment includes measuring electrocardiogram (ECG) signals for a first occupant located in a first environment; sampling comfort data from the first occupant while measuring the ECG signals using a comfort scale, wherein the comfort scale includes a plurality of discomfort values and a plurality of comfort values; converting the ECG signals to inter-beat intervals; generating N heart rate variability (HRV) parameters based on the inter-beat intervals, where N is an integer greater than one; assigning at least some of the plurality of comfort values to a discomfort state, wherein the discomfort state also includes the plurality of discomfort values; assigning remaining ones of the plurality of comfort values to a comfort state; and defining a comfort classification model in N-dimensional HRV parameter space based on the discomfort state and the comfort state.

In other features, the method includes generating an electrocardiogram (ECG) signal for a second occupant of a second environment; identifying inter-beat intervals based on the ECG signal; and controlling a heating, ventilation and air conditioning (HVAC) system based on the inter-beat intervals and the comfort classification model.

In other features, the second environment comprises a vehicle interior and the HVAC system includes a fan, a heater and an air conditioner. The method includes controlling at least one of a seat heater, a seat heater/cooler and a steering wheel heater based on the inter-beat intervals and the comfort classification model.

In other features, the method includes comparing variations in the inter-beat intervals to a predetermined variation threshold; controlling the HVAC system using a temperature setpoint when the variations are greater than the predetermined variation threshold; and controlling the HVAC system using the inter-beat intervals and the comfort classification model when the variations are less than the predetermined variation threshold.

In other features, the method includes generating N heart rate variability (HRV) parameters based on the inter-beat intervals, where N is an integer greater than one, wherein the comfort classification model is defined in N-dimensional HRV parameter space.

In other features, the comfort classification model defines at least one comfort region in the N-dimensional HRV parameter space and at least one discomfort region in the N-dimensional HRV parameter space.

In other features, the N HRV parameters include linear statistical parameters. The N HRV parameters include non-linear statistical parameters. The N HRV parameters include linear and non-linear statistical parameters.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 1 is a functional block diagram of an example of an HVAC system that is controlled based on occupant heart rate variability (HRV) parameters according to the present disclosure;

FIG. 2 is a side view of an example of an occupant in a vehicle and example locations of HRV sensors;

FIG. 3 is a functional block diagram of an example of a HRV sensor system including radio frequency identification (RFID) tags and an RFID reader according to the present disclosure;

In the drawings, reference numbers may be reused to identify similar and/or identical elements.

DETAILED DESCRIPTION

Figure 4:
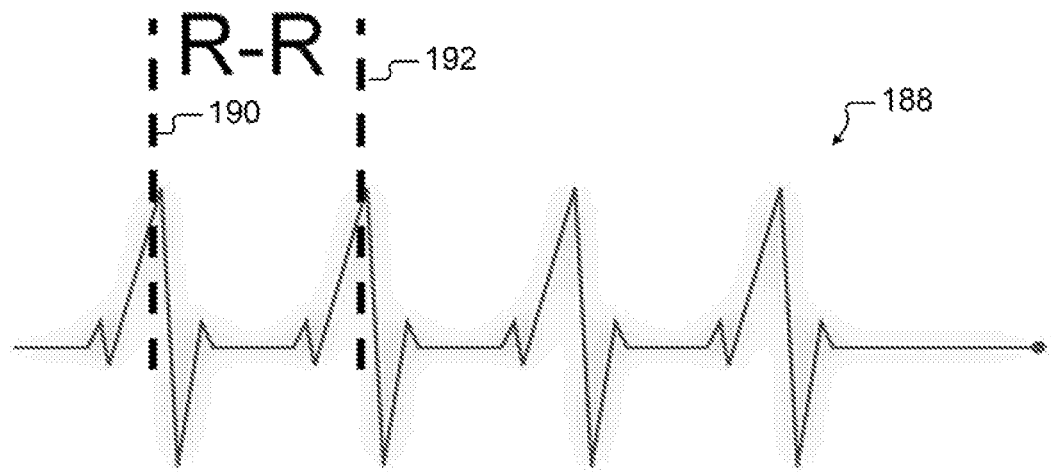
FIG. 4 is a graph showing an ECG and identification of successive heart beats to determine inter-beat interval (RR)

Systems and methods according to the present disclosure control temperature in an environment such as a vehicle, room or space using a HVAC system (and/or one or more micro-climate such as heated and cooled seats) to achieve occupant comfort based upon one or more sensed heart rate variability (HRV) parameters, HRV entropy and/or other environmental parameters (such as temperature and/or humidity in the environment and/or ambient temperature and/or humidity outside). While the foregoing description will be described in conjunction with an HVAC system, the HRV parameters may also be used to control the micro-climates as well.

The autonomic nervous system includes the sympathetic nervous system and the parasympathetic nervous system. Variations in occupant comfort can be detected using changes in the autonomic nervous system. HRV of an occupant of a vehicle, room or space is a good indicator of operation of the autonomic nervous system. The systems and methods described herein correlate HRV parameters to thermal comfort. HRV parameters can be correlated to sympathetic nervous system attributes such as skin comfort and/or other attributes of the human autonomic system such as homeostasis.

Referring now to FIG. 1, an example of a HVAC system 100 in a vehicle is shown. The HVAC system 100 includes an HVAC controller 120 that controls operation of the HVAC system 100 based upon HVAC user input devices 122 and sensed HRV parameters of one or more occupants located in one or more zones.

In some examples, the HVAC system also includes one or more micro-climate systems or zones that form part of the HVAC system. In other examples, the micro-climate systems include additional standalone systems (in addition to the HVAC system) that are also controlled using one or more HRV parameters. For example, temperature controlled seats can be used in addition to the HVAC system to achieve occupant comfort.

In some examples, the HVAC user input devices 122 include one or more rotatable knobs, buttons, touchscreens, sliders, smartphones, or other suitable controls for setting fan speed, temperature set points, etc. for the entire vehicle, room or space and/or one or more microclimates within the vehicle.

The HVAC system 100 further includes one or more temperature sensors 124 and/or humidity sensors 126 for sensing environmental temperature and humidity and/or ambient temperature and/or humidity. The temperature sensors 124 and/or humidity sensors 126 may be located within the interior of the environment and/or outside of the environment.

When operating conventionally, the HVAC system 100 is controlled based on differences between a temperature set point and a sensed temperature. This form of control is independent of the actual comfort of the occupants in the environment. As will be described further below, the systems and methods described herein monitor one or more HRV parameters of the occupant. The comfort of the occupant is also used to control operation of the HVAC system for the environment. Depending upon the situation, the systems and methods described herein control the HVAC system using only the temperature set points, only the HRV parameters and/or a combination of both the temperature set points and the HRV parameters.

The HVAC system 100 typically includes one or more fans 128 to direct recirculated air or external air through ducts (not shown) into the environment. One or more heaters 130 may be used to heat the air flowing through the ducts and into the cabin. The HVAC system 100 further includes an air-conditioning (AC) system 132 to cool the air flowing through the ducts and into the environment. For example, the AC system 132 typically includes a compressor, an evaporator, a condenser, and/or other AC components (all not shown). As can be appreciated, occupant comfort may also be affected by additional heating or cooling components such as seat heaters/coolers 136 and/or a steering wheel heater 140, which may also be controlled to increase occupant comfort based on one or more HRV parameters.

A HRV sensor system 144 generates an electrocardiogram (ECG) and/or monitors one or more HRV parameters for one or more occupants of the vehicle. The HRV sensor system 144 provides feedback from the occupant to the HVAC controller 120. The HRV sensor system 144 may generate the ECG data and/or sense one or more HRV parameters using any type of HRV sensor. In some examples, the HRV sensor system 144 includes standalone HRV sensors. In other examples the HRV sensor system 144 includes two or more devices (such as an RFID sensor and an RFID reader) that cooperate to generate ECG and/or HRV signals. Examples of suitable HRV sensor systems include photoplythesmograph (PPG) sensors that sense one or more HRV parameters based on skin contact. Other sensors include radar-type detection of HRV parameters using sound wave backscattering and/or high frequency Doppler signals. Still other sensors include ECG sensors that are located in the seat in proximity to the occupant (such as in air bladders or interwoven in fabric, radio frequency identification (RFID) sensors located in seat belts, in the back of the seat, or in other locations).

In some examples, the RFID system may be similar to the system described in "Monitoring Vital Signs Over Multiplexed Radio by Near-Field Coherent Sensing", Nature Electronics, 1997, X. Hui and E. Kan, which is hereby incorporated by reference in its entirety.

In some examples, the HVAC controller 120 includes a HRV monitor controller 148 including a HRV analysis module 152. The HRV analysis module 152 receives the ECG and/or HRV parameters and adjusts HVAC operation based at least in part upon the ECG and/or one or more HRV parameters. While the HVAC controller 120 is shown to include the HRV monitor controller 148, the HRV monitor controller 148 can be arranged as a standalone controller (for example, as shown in FIG. 3) or integrated with another vehicle controller.

Referring now to FIG. 2, an occupant 158 is shown seated in a seat 160 of a vehicle. While a vehicle is shown, the occupant can be located in a room of a building or a smaller space such as a cubicle. The seat 160 is shown to include a seat portion 162, a backrest portion 164 and/or a headrest portion 166. The HRV sensor system 144 may include one or more HRV sensors that are located near the occupant 158. For example, the HRV sensors can be embedded in one or more of the seat portion 162, the backrest portion 164, and/or the headrest portion 166. For example, an array of sensors 170 may be arranged in the backrest portion 164 adjacent to an occupant's heart location to generate an ECG. Additional locations include touch sensors in a steering wheel 176, RFID sensors 172 located in a seat belt 178, etc. In some examples, the RFID sensors 172 are arranged in a portion of the seatbelt 178 located within a few inches of a heart location of the typical occupant. The sensors can be hardwired sensors or wireless sensors. In some examples, the HRV sensor is integrated with a smartphone or other wearable device such as a fitness monitor.

Referring now to FIG. 3, in some examples, one or more radio frequency identification (RFID) sensors or tags 180-1, 180-2, . . . , and 180-S (collectively RFID sensors 180) (where S is an integer) may be used to generate an ECG and/or monitor HRV parameters of one or more occupants. A local controller and memory (not shown) may also be provided for signal storage and processing. Each of the RFID sensors 180 includes a transmitter and a receiver. An RFID reader 182 periodically transmits an interrogation signal to the RFID sensors 180 that provides power to the RFID sensors 180. The RFID sensors 180 are temporarily powered by the interrogation signal, make an ECG and/or HRV parameter measurement and transmit the ECG or HRV parameter measurement to the RFID reader 182 prior to shutting down. Alternately, the RFID sensors 180 can process the raw ECG signal and send a processed signal prior to transmission to the RFID reader 182.

Referring now to FIG. 4, an example of an ECG signal and a HRV parameter is shown. In this example, the HRV parameter includes sampling the ECG signal to identify adjacent heart beats (R) to establish an inter-beat interval (RR) of an occupant or a heart rate in beats per minute. In some examples, the ECG signal sample spans a period greater than or equal to two or more adjacent heartbeats.

The ECG signal is sent to the HRV analysis module 152 and is processed to generate one or more processed HRV parameters, i.e. a processed RR (PRR) signal. In addition to the inter-beat intervals (RR) and/or heart rate per minute, the HRV parameter may include other parameters. Examples of other HRV parameters include mean time between adjacent heart beats (or mean RR interval), a square root of the mean of the sum of differences of successive RR intervals, a standard deviation of a difference between adjacent RR intervals, and/or a percentage of adjacent RR pairs that differ by a predetermined period (such as a number of milliseconds) during a predetermined period.

In addition to the foregoing HRV parameters, analysis of the ECG signal may be performed in the frequency domain to provide total spectral power within a predetermined bandwidth and/or spectral power in one or more predetermined ranges. For example, the total spectral power from 0-0.4 Hz can be determined. Other ranges may include a very low frequency range such as frequencies from 0.003 to 0.04 Hz, a low range of frequencies such as frequencies from 0.05 to 0.15 Hz, and a high range of frequencies such frequencies greater than 0.15 Hz. Other HRV parameters may include a ratio of power in low and high power ranges. Further non-linear analysis may include the processing of a Poincaré return map or processing of a periodogram of the RR signal as a function of time, e.g. Lomb-Scargle periodogram, chi-square periodogram, etc.

In some examples, signal entropy (a measure of variation in one or more parameters of the ECG signal and/or HRV parameters) may be used as a factor in determining when to start monitoring and/or using HRV parameters to control the HVAC system. In other words, initial temperature control may be performed based on temperature set points until signal entropy falls below a predetermined entropy threshold. Once signal entropy falls below the predetermined entropy threshold (and the HRV settles), comfort-based control based on HRV parameters can be used.

Additional HRV parameters are described in "Heart Rate Variability as a Predictive Biomarker of Thermal Comfort", Journal of Ambient Intelligence and Humanized Computing, K. Nikurikiyeyezv, Y. Suzuki ang G. Lopez, which is hereby incorporated by reference in its entirety.

Figure 5:
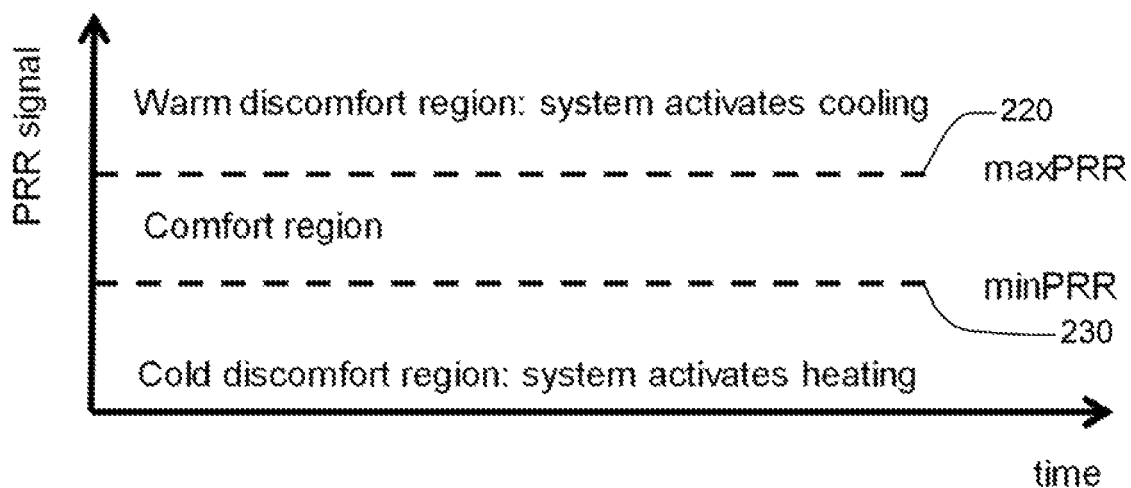
FIG. 5 is a graph illustrating an example of a HRV parameter as a function of time and max and min HRV thresholds according to the present disclosure.

Referring now to FIG. 5, the analysis module establishes maximum and minimum HRV thresholds. For example, maximum and minimum PRR thresholds (maxPRR threshold 220 and minPRR threshold 230) may be used. In some examples, the maximum and minimum HRV thresholds are statistically defined and/or determined after a training period for a single occupant or groups of occupants. When the maximum HRV threshold is exceeded, the occupant is in a warm discomfort region and the HR controller activates the HVAC system for cooling. When the minimum HRV threshold is exceeded, the occupant is in a cold discomfort region and the HR controller activates the HVAC system for heating.

Figure 6:
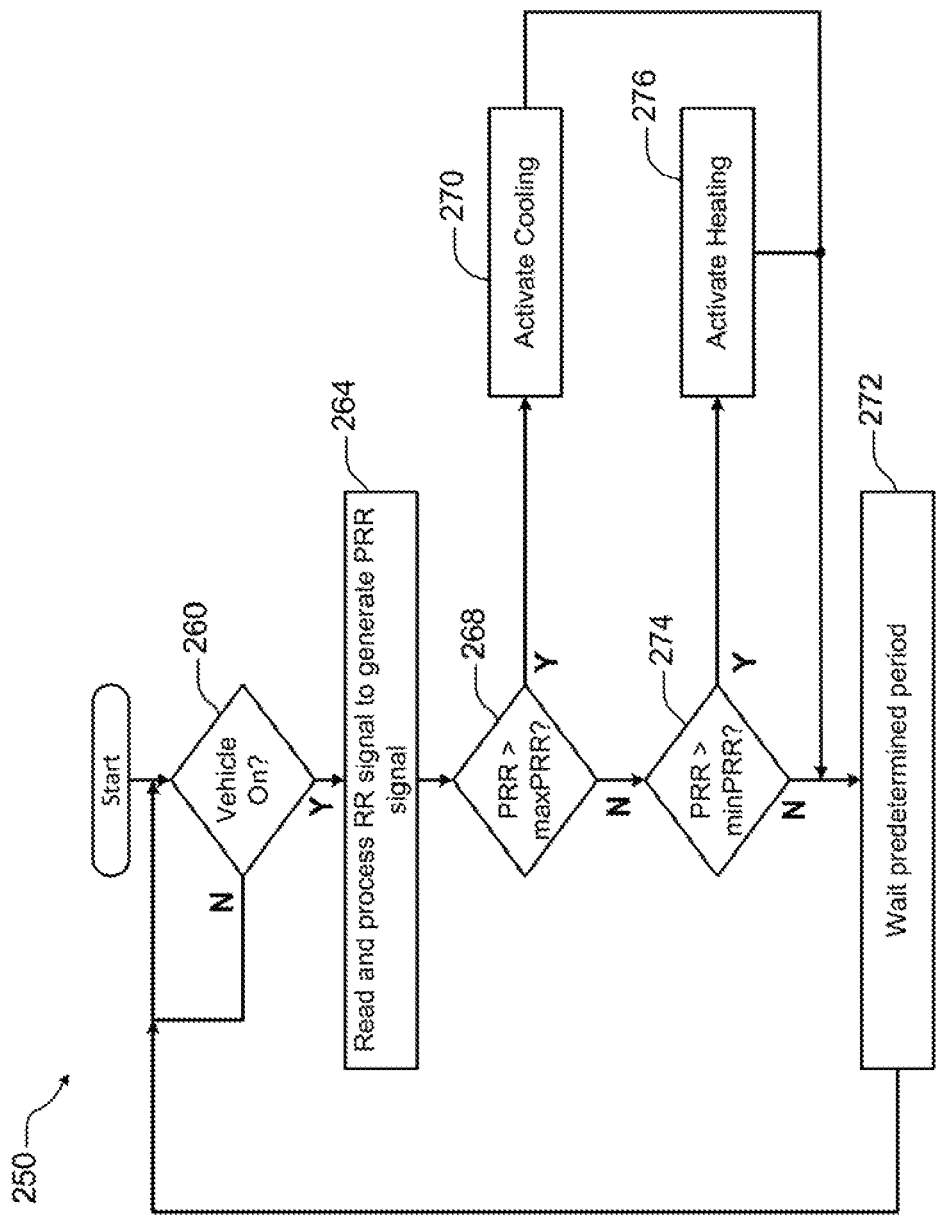
FIG. 6 is a flowchart illustrating an example of a method for controlling the HVAC system based upon the HRV parameters according to the present disclosure.

Referring now to FIG. 6, a method 250 for controlling the HVAC system based upon the HRV parameters is shown. While the foregoing examples in FIGS. 6, 7, 9 and 10 specifically refer to PRR, maxPRR and minPRR thresholds, the method applies to other HRV parameters, thresholds and/or N-dimensional spaces. At 260, the method determines whether the vehicle (or the HVAC system) is ON. In some examples, the vehicle is ON when the ignition switch or accessory switch is switched ON. However, other vehicles such as electric vehicles may include other criteria for determining when the vehicle or the HVAC system is ON.

When 260 is true, the method continues at 264 and reads and processes the RR signal to generate the PRR signal. At 268, the PRR signal is compared to the maxPRR threshold. If the PRR signal is greater than the maxPRR signal, the HVAC system is activated to provide cooling at 270. After a predetermined period in 272, the method returns to 260. If 268 is false, the method continues with 274. At 274, the PRR signal is compared to the minPRR threshold. If the PRR signal is less than the minPRR signal, the HVAC system is activated to provide heating at 270.

Figure 7:
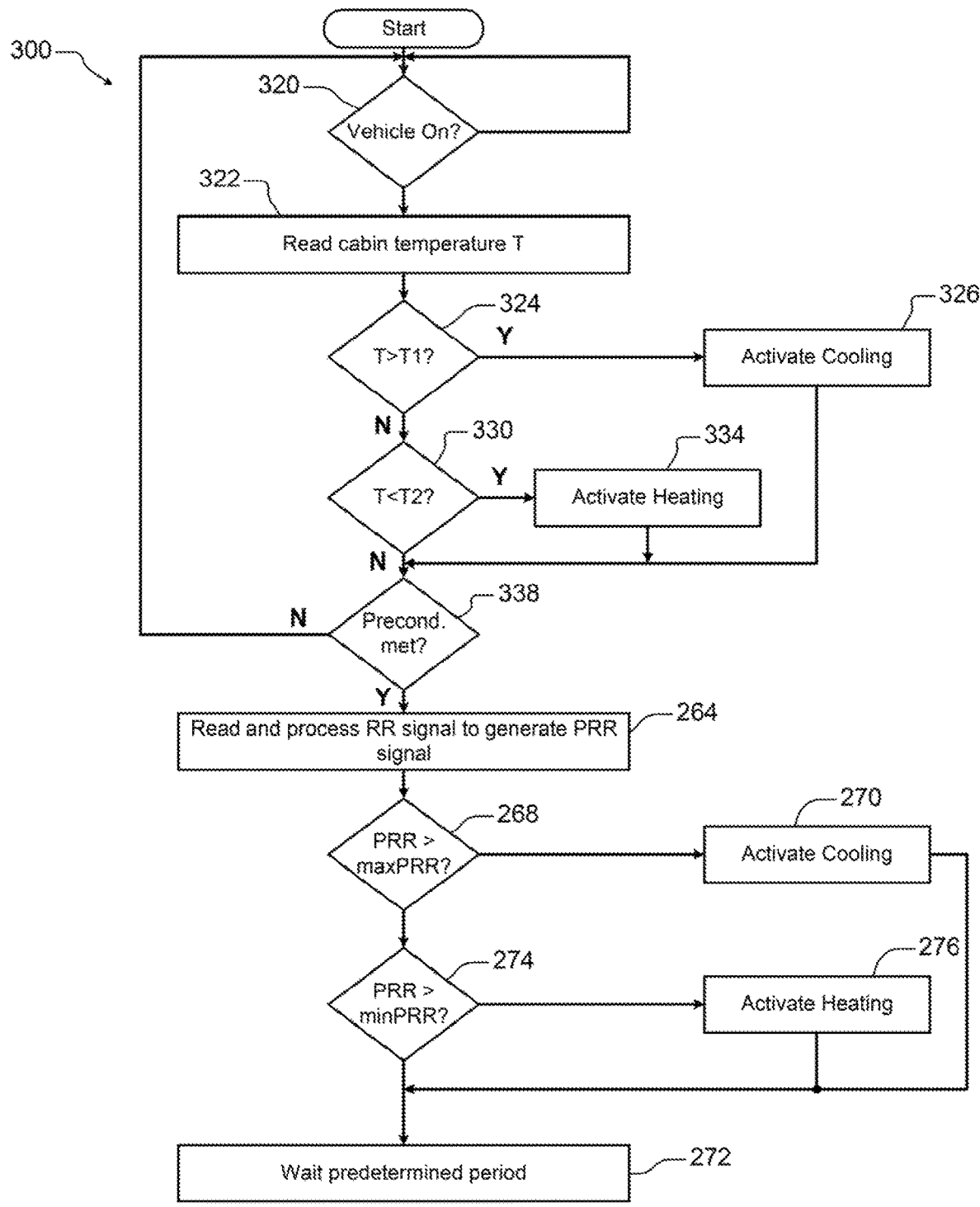
FIG. 7 is a flowchart illustrating another example of a method for controlling the HVAC system based upon the HRV parameters according to the present disclosure.

Referring now to FIG. 7, another method 300 for controlling the HVAC system is shown. The HVAC system may be initially controlled based solely on temperature set points until one or more preconditions are reached. In some examples, the preconditions include reaching a predetermined period. In other examples the preconditions include reaching a predetermined temperature set point. In still other examples, the precondition includes other factors such as entropy in the HR signal falling below a predetermined entropy value.

At 320, the method determines whether the vehicle or the HVAC system is on. At 322, the cabin temperature is read. At 324, the method determines whether the cabin temperature is greater than a first predetermined temperature T1. If 324 is true, the method activates the HVAC system to provide cooling at 326. If 324 is false, the method determines whether the cabin temperature is less than or equal to a second predetermined temperature T2 at 330. If 330 is true, the method activates the HVAC system to provide heating at 334. Control continues from 326, 330 (if false), and 334 with 338 where the method determines whether preconditions for transitioning to HRV-based control have been met. If 338 is false, the method returns to 320. If 338 is true, the method continues at 264 as described above in FIG. 6.

Figure 8:
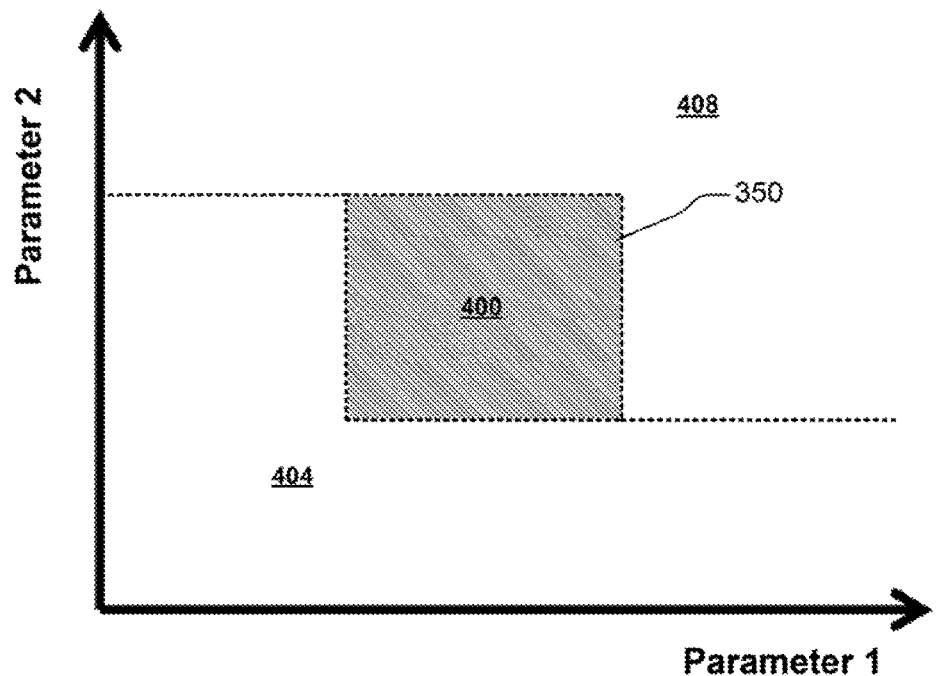
FIG. 8 is a graph showing an example of first and second HRV parameters that define a 2-dimensional comfort space and maximum and minimum HRV parameter spaces according to the present disclosure.

While some of the preceding examples described the use of a single HRV parameter and single pair of maxPRR and minPRR values, the HR monitor controller may use N HRV parameters. The N HRV parameters define an N dimensional space where N is an integer greater than one. In addition, N-dimensional maxPRR space(s) and minPRR space(s) may also be defined to correspond with the N HRV parameter space. For example in FIG. 8, N=2 and two parameters are used to define a two-dimensional space. In this example, at least one two dimensional maxPRR space 404 and at least one two-dimensional minPRR space 408 are also defined.

Figure 9:
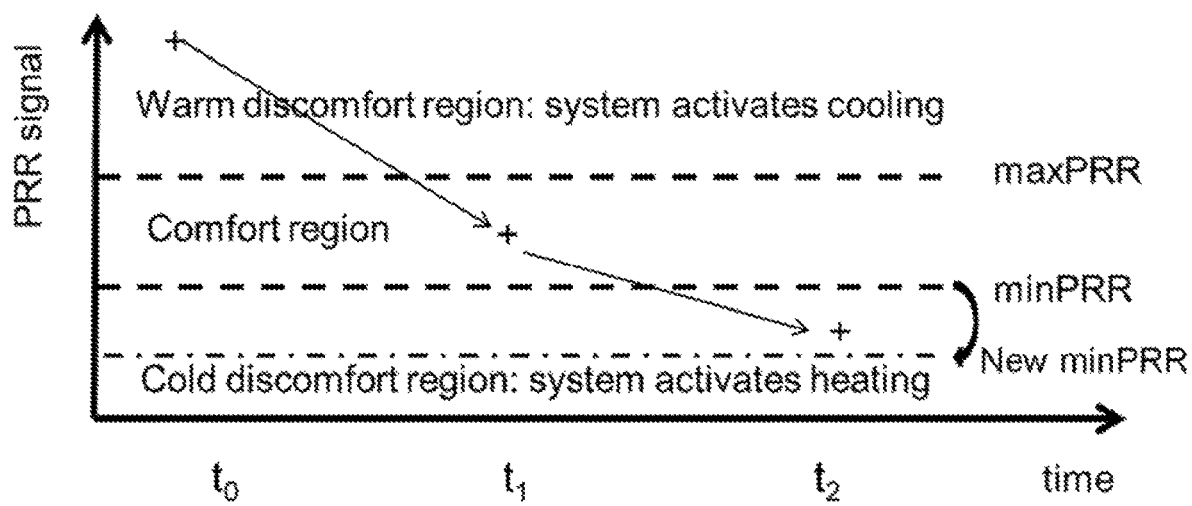
FIG. 9 is a graph illustrating an example of a HRV parameter as a function of time and adaptive maximum and minimum HRV thresholds according to the present disclosure.

Referring now to FIG. 9, the maxPRR and/or minPRR thresholds may be adjusted by the analysis module under certain circumstances. In the example in FIG. 9, the system activates cooling at t0 and the system stops cooling at t1. During periods before t2, the HR monitor controller uses a first pair of minPRR and maxPRR values. During operation at t1, the HR monitor controller establishes comfort given the first pair of minPRR and maxPRR threshold values. However, after the HVAC system is turned off, the occupant may activate heating when the occupant is still not warm enough. The HR monitor controller monitors operation of the HVAC system, cabin temperatures and/or humidity levels, and monitors when the system is turned off. The analysis module adjusts at least one of the minPRR and maxPRR threshold values (in this case the minPRR value) and uses the adjusted minPRR and/or maxPRR threshold values for subsequent periods.

Figure 10:
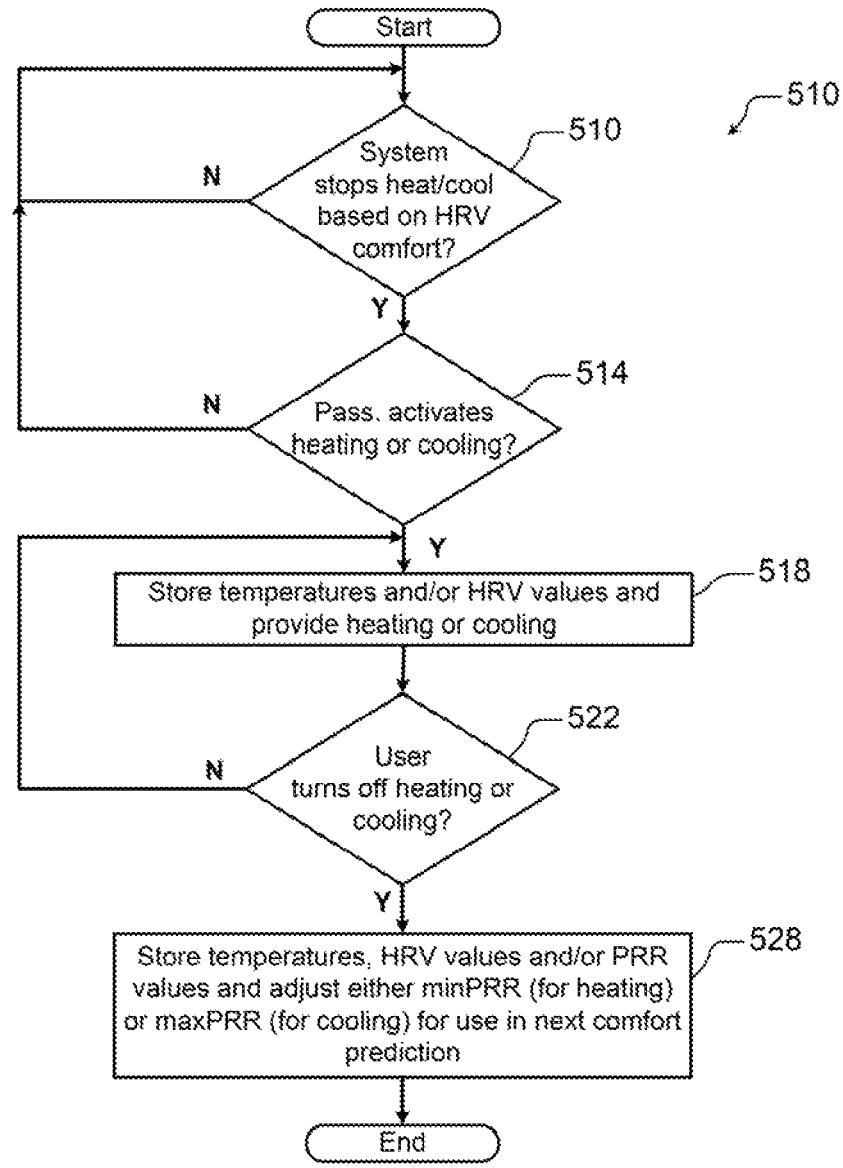
FIG. 10 is a flowchart illustrating an example of a method for adapting at least one of the maximum and minimum HRV thresholds according to the present disclosure.

Referring now to FIG. 10, a method 500 for adjusting one or more maxPRR or minPRR threshold values is shown. At 510, the method determines whether the system stops heating or cooling based on HRV comfort control. When 510 is true, the method determines whether the user reactivates heating or cooling at 514. When 514 is true, the temperatures and/or humidity values are stored and heating or cooling is provided based on the request. At 522, the method determines whether the user turns off the heating or cooling (or whether a heating or cooling set point is reached). When 522 is true, the method stores temperatures and/or PRR values and adjusts at least one of the maxPRR threshold value or space or the minPRR threshold value or space at 528 and the method ends.

As can be appreciated, controlling the HVAC system of a vehicle offers a variety of benefits. The approach allows personalization of comfort and optimization of the corrective power of HVAC (corresponding to reduced usage) per occupant. As used herein, personalization refers to individuality (e.g. male vs female or 3 occupants in the cabin as opposed to 5 occupants. Personalization also refers to individuality and preferences of thermal comfort.

The approach also allows personalization independent of health condition, age, and/or gender. The approach also allows thermal comfort to children. The operation of the system will therefore reduce $CO_2$ and may provide $CO_2$ credit benefits for original equipment manufacturers (OEMs).

Other potential benefits for the OEMs include the ability to reduce the size of the HVAC system. As a result, the mass of refrigerant that is used can be reduced. Additional advantages include increased range in all EV powertrains, scalability of thermal comfort products, increased customer satisfaction and other benefits.

Figure 11:
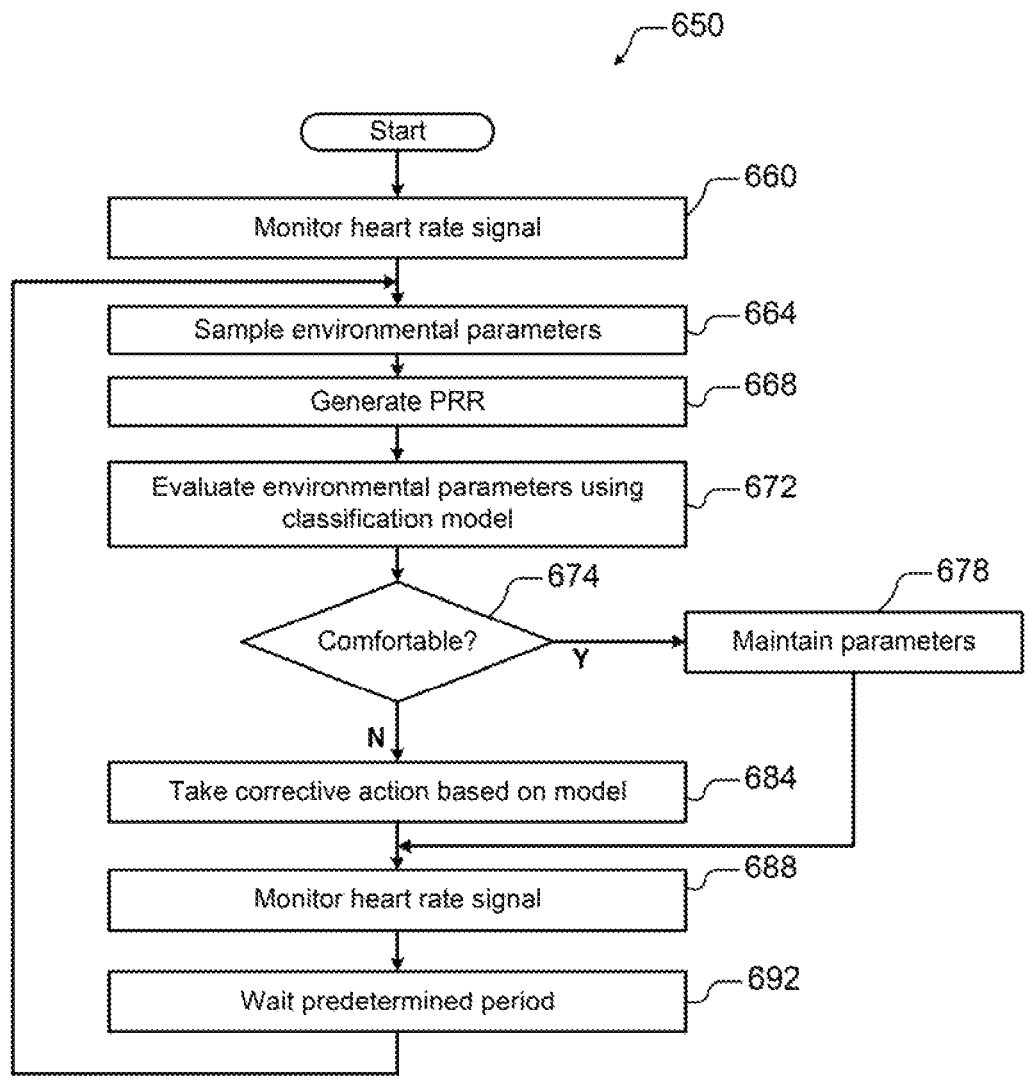
FIG. 11 is a flowchart illustrating another example of a method for controlling the HVAC system based upon the HRV parameters according to the present disclosure.

Referring now to FIG. 11, a method 650 for controlling the HVAC system based upon the PRR or HRV parameters is shown. At 660, the method monitors an ECG or heart rate signal. At 664, the method samples environmental parameters. Examples of the environmental parameters include temperature, air velocity around the occupant, humidity, sun load, clothing insulation, etc.

At 668, the method generates the PRR. At 672, the method evaluates environmental parameters and the PRR using the classification model to determine the comfort/discomfort state of the occupant. The classification model includes a matrix with all of the HRV statistical parameters that are needed to classify the PRR and the set of environmental parameters that are input. The classification model may perform classification using a multilevel scale (very uncomfortable, slightly uncomfortable, slightly comfortable or very comfortable) or a binary scale (comfort/discomfort). At 674, the method determines whether the occupant is comfortable.

If the occupant is comfortable as determined at 674, the method maintains HVAC control parameters (e.g. the operating mode (heating or cooling), temperature setting, fan velocity, etc. are maintained) at 678. If 674 is false, the method takes corrective action by changing one or more of the HVAC control parameters based on the classification model at 684. The method continues from 678 and 684 at 688. At 688, the method monitors the heart rate signal. At 692, the method waits a predetermined period and then returns to 664.

Figure 12:
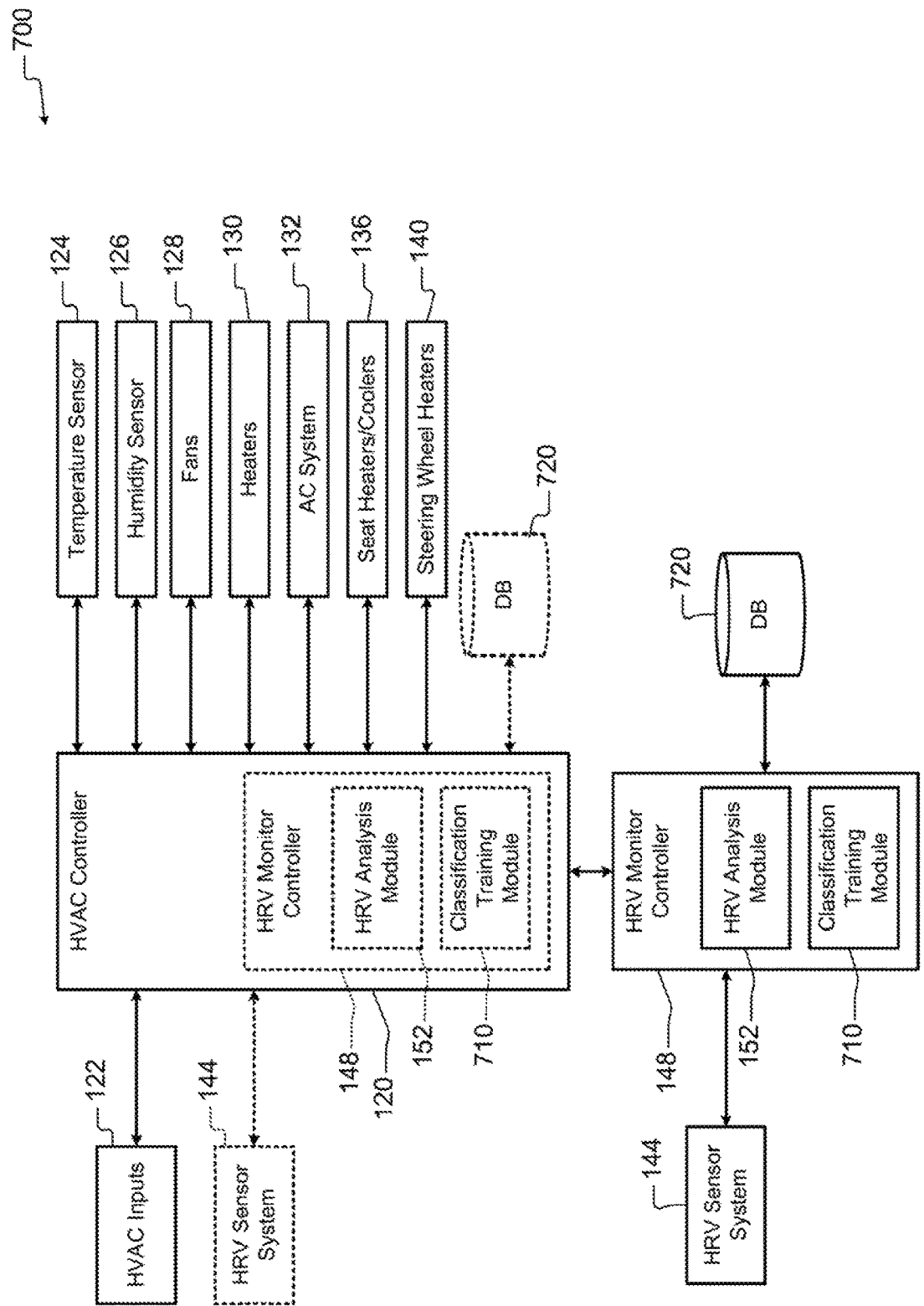
FIG. 12 is a functional block diagram of an example of an HVAC system that is controlled based on occupant HRV parameters and that performs localized classification training according to the present disclosure.
Figure 13:
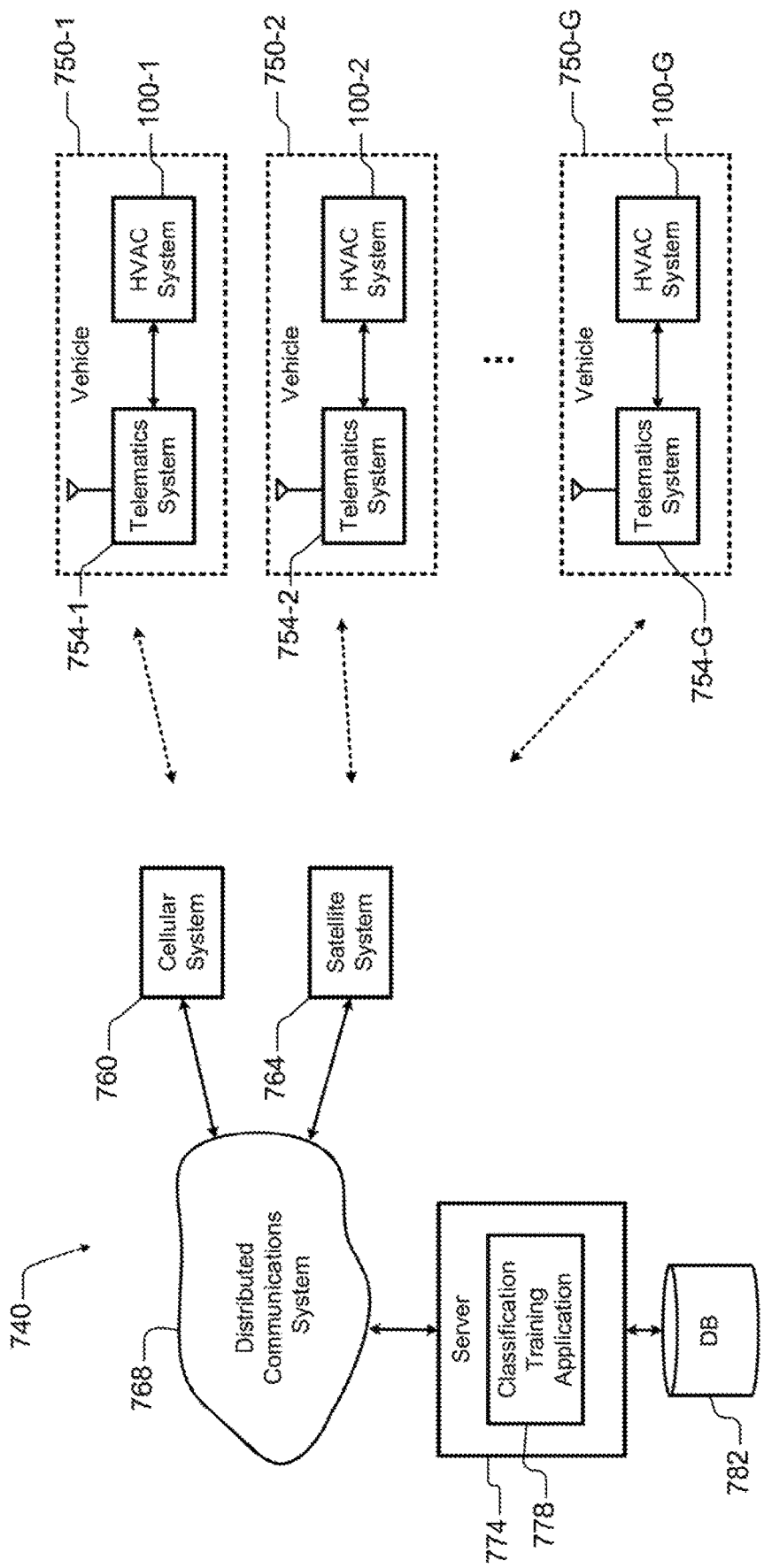
FIG. 13 is a functional block diagram of an example of an HVAC system that is controlled based on occupant HRV parameters and that performs remote or cloud-based classification training according to the present disclosure.

Referring now to FIGS. 12 and 13, an HVAC system 700 can perform localized or remote training of the classification model based on manual setpoint changes made by the occupant to the HVAC system. In other words, when the occupant manually changes a setpoint or desired operating state of the HVAC system, it can be reasonably presumed that the occupant is making a change in a direction towards increased comfort. This fact can be used to improve the classification model through classification training. The classification training can be performed locally in the vehicle as shown in FIG. 12 or the relevant data (HRV parameters, environmental data, and data relating to the HVAC setpoint changes) can be transmitted remotely to a cloud-based system for further analysis as shown in FIG. 13.

Referring back to FIG. 12, the HVAC system 700 optionally includes the HVAC controller 120 including the HRV monitor controller 148. The HRV monitor controller 148 may optionally include the HRV analysis module 152 and a classification training module 710. Data such as the HRV data, the environmental data, and data relating to the HVAC setpoint changes may be stored in a database 720 that is associated with the HVAC controller 120. Alternately, the HRV monitor controller 148, the HRV analysis module 152, and the classification training module 710 are implemented as standalone devices that are located in the vehicle but remotely from the HVAC controller 120. When a sufficient amount of data is collected, the classification model is trained by the new data and the classification model is adjusted.

While classification training can be performed locally as shown in FIG. 12, the classification training can be performed on a wider set of data (which may or may not include data from other vehicles) by transmitting the HRV data and environmental data to a remote server. After training, updates to the classification model can be sent back to the vehicle from the remote server.

Referring back to FIG. 13, a plurality of vehicles 750-1, 750-2, . . . , and 750-G (collectively vehicles 750) include HVAC systems 100-1, 100-2, . . . , and 100-G (collectively HVAC systems 100) and telematics systems 754-1, 754-2, . . . and 754-G (collectively telematics systems 754), respectively (where G is an integer greater than one). The telematics systems 754 wirelessly transmit data including HRV parameters, environmental data and/or HVAC setpoint changes remotely via a cellular system 760 or a satellite system 764. The cellular system 760 or the satellite system 764 are connected by a distributed communications system 768 such as the Internet to a server 774 that includes a classification training module 778 and a database 782. In some examples, the classification training module 778 makes changes to the classification model based on the data received from multiple vehicles and then transmits the classification model back to the vehicle. In other examples, training of the classification models may be limited to similar model vehicles, vehicles in similar geographical regions, etc.

Figure 14:
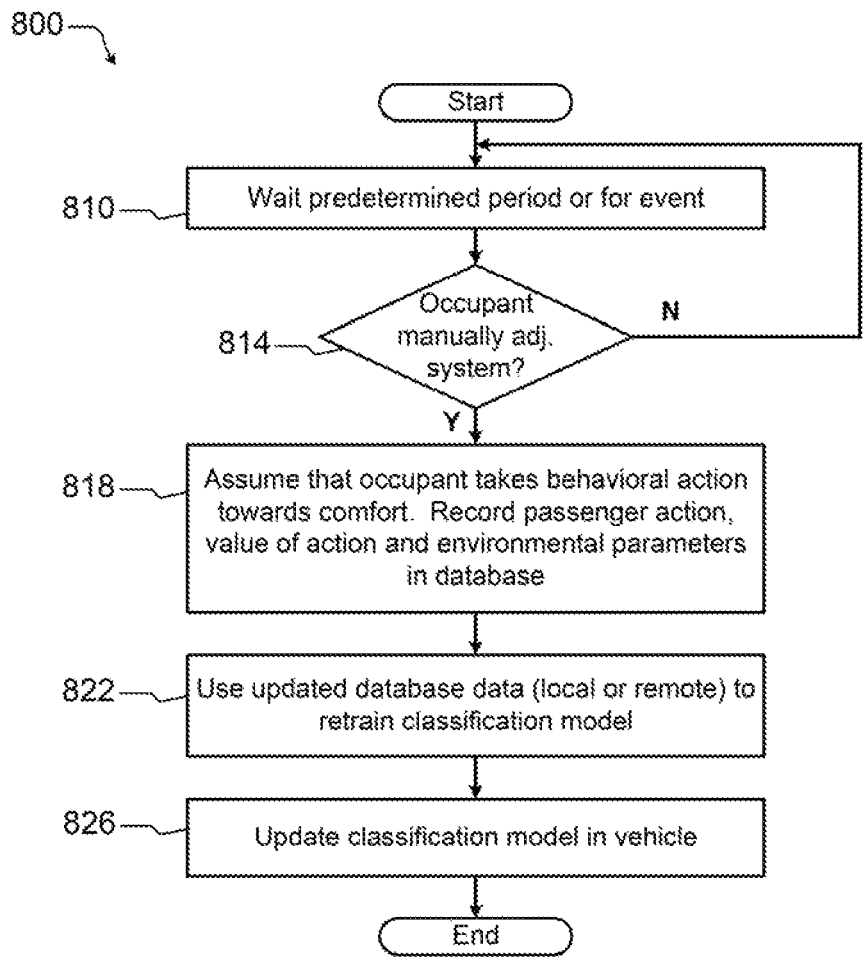
FIG. 14 is a flowchart illustrating an example of a method for controlling the HVAC system based upon the HRV parameters and updating classification training according to the present disclosure.

Referring now to FIG. 14, a method 800 for controlling updating the classification model after training is shown. At 810, the method waits a predetermined period (or for an event to occur). At 814, the method determines whether the occupant manually changes a setpoint of the HVAC system. If 814 is false, the method returns to 810. When 814 is true, the method assumes that the occupant takes behavioral action in a direction towards increased comfort. The occupant's actions are recorded along with the value or magnitude of the action (temperature change amount or fan speed change amount) and current PRR or HRV parameters and/or environmental data. The data is stored and analyzed either locally (FIG. 12) or remotely (FIG. 13). At 822, the data is used to retrain the classification model. At 826, after the retraining, the classification model in the vehicle is updated.

Figure 15:
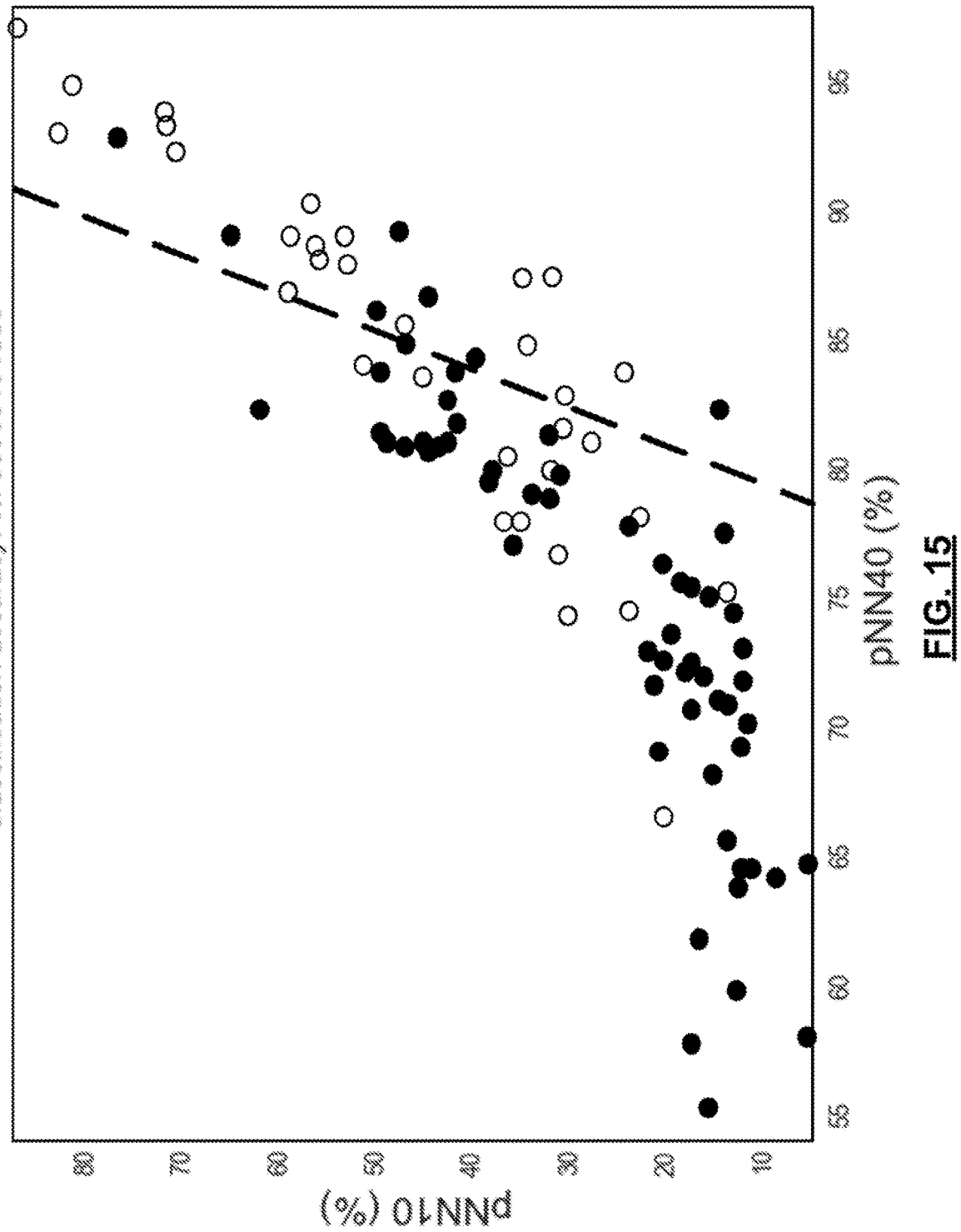
FIG. 15 is a graph illustrating comfort data as a function of first and second HRV parameters and a classification model based on the comfort data.
Figure 16:
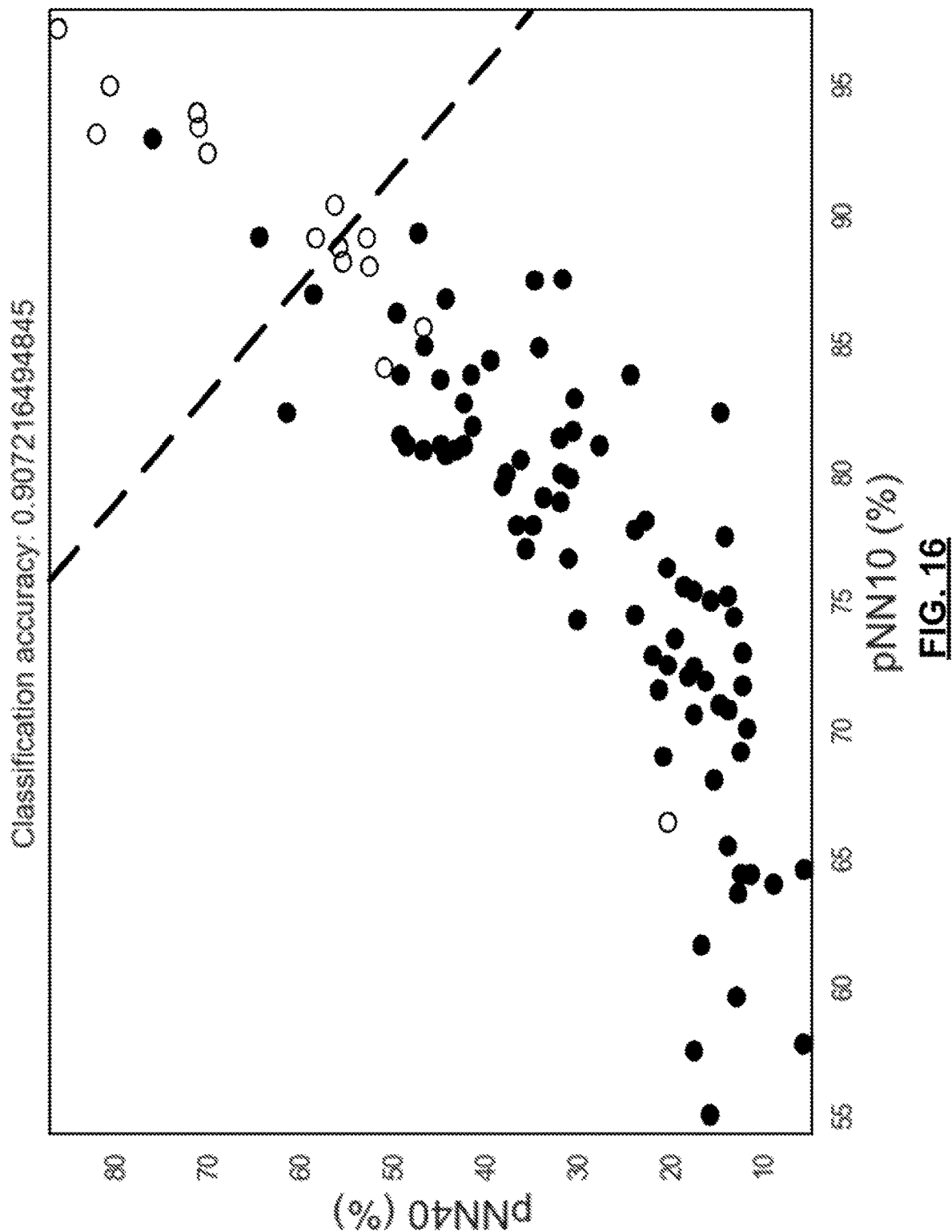
FIG. 16 is a graph illustrating modified comfort data as a function of first and second HRV parameters and another classification model based on the comfort data according to the present disclosure.
Figure 17:
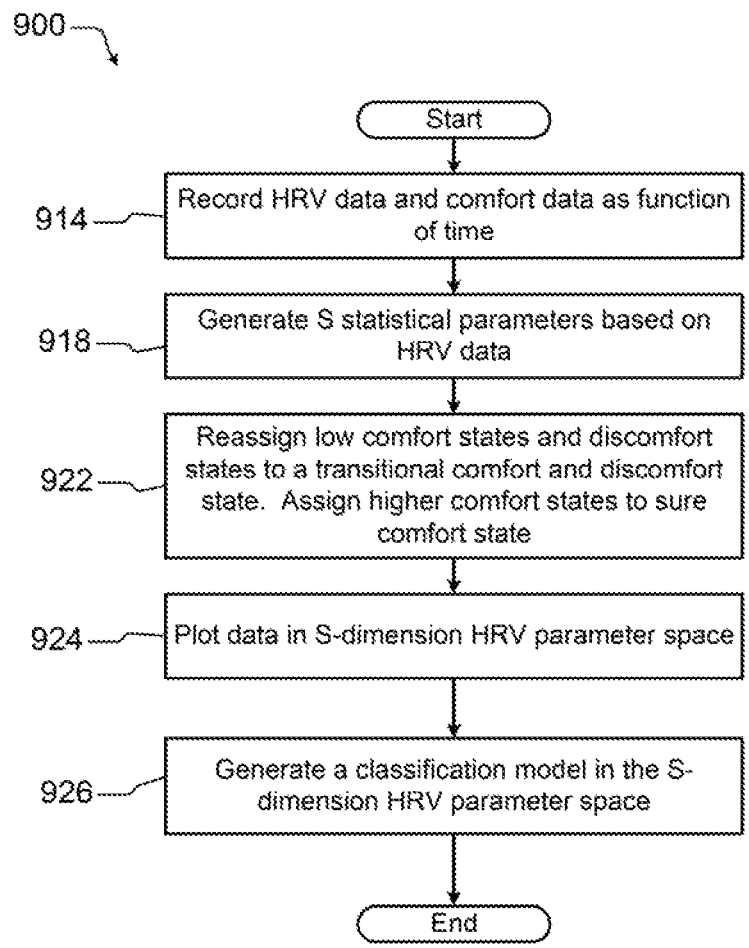
FIG. 17 is a flowchart of a method for generating the modified comfort data as a function of first and second HRV parameters and a classification model based on the comfort data according to the present disclosure.

Referring now to FIG. 15-17, techniques can be used to improve the accuracy of the classification model. In FIG. 15, a graph illustrates data samples as a function of first and second HRV parameters. Based on the samples, a classification model is defined to differentiate between comfort and discomfort regions in the 2-dimensional HRV parameter space.

For example, sample data can be generated using a linear comfort scale between a negative number and a positive number (having the same magnitude as the negative number). Positive numbers represent increasing comfort. Negative numbers represent increasing discomfort. For example, the scale can include a range from −4 to +4 (such as the Berkeley Comfort Scale).

In this example, the HRV parameters that are selected for the classification model include pNN10% and pNN40%, although any other HRV parameters can be used. As can be seen in FIG. 15, the classification model is defined based on the sample comfort data. For example, least means squares and/or other techniques can be used to identify a position and slope of the dotted line separating comfort and discomfort regions. In this example, a binary classification model is used and the discomfort region is defined by the classification model to the left of the dotted line in FIG. 15. The comfort region is defined by the classification model to the right of the dotted line in FIG. 15. For this data set, the classification model has an accuracy of 78.35%. In other words, based on the dotted line, some discomfort samples are located in the comfort region of the classification model and some comfort samples are located in the discomfort space of the classification model. As can be appreciated, the classification model preferably minimizes this type of misclassification since the classification model will be used to control the HVAC system.

In FIG. 16, examples of steps that can be taken to improve or optimize the accuracy of the classification model (for the same data shown in FIG. 15). In some examples, new states (other than pure comfort and discomfort states) are defined and used. Rather than using the strict comfort states corresponding to positive and negative values, a first new state (or sure comfort state) includes comfort values $>=+1$ and a second new state or discomfort to slight comfort state includes values −4 to <+1. Using these modified states, a modified classification model shown in FIG. 16 can be defined. The new classification model has accuracy that is improved relative to that shown in FIG. 15. For this data set, the modified classification model now has an accuracy of 90.72%. While the examples of classification models in FIGS. 15 and 16 use linear HRV parameters, the classification models may use linear and non-linear HRV parameters or both non-linear parameters.

Referring now to FIG. 17, a method 900 for generating the modified comfort data described above is illustrated. At 914, HRV parameters, environment data and comfort data are recorded. In some examples, a linear comfort scale such as the Berkeley Comfort Scale from −4 to +4 is used. At 918, S HRV statistical parameters are generated based on the HRV data (where S is an integer greater than or equal to two). The S HRV statistical parameters can be linear or non-linear HRV statistical parameters.

At 922, very low comfort states such as 1 are reassigned to a new state that also includes 0 and discomfort states. Higher comfort states are reassigned to a sure comfort state. For example, a first state or "sure comfort" state includes comfort values from >+1 to +4. A second state or "discomfort to slight comfort" state includes values from −4 to <=+1. At 924, the comfort data is plotted in the S-dimension HRV parameter space using the new comfort classifications. At 926, a classification model (to classify comfort or discomfort states in the S-dimension HRV parameter space) is generated based on the new comfort states.

In this example, the classification model defines a line or S-dimensional shape in the S-dimensional HRV parameter space. In this example, S=2 and the model generates a decision based on values of the first HRV parameter and the second HRV parameter. As can be appreciated, the accuracy of the model is improved by the foregoing techniques. While classification models using two HRV parameters are shown in the examples above, the classification model can include more than two HRV parameters.

While the foregoing description relates to vehicles, the present disclosure can also be used to control thermal comfort in other environments. For example, thermal comfort can be used to control thermal comfort in a building (such as an office, home, and/or workspace). Additional examples include the use of thermal comfort to control a medical device and/or in medical applications.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A temperature control system, comprising:
   a heating, ventilation and air conditioning (HVAC) system configured to control temperature in an environment;
   a sensor configured to generate an electrocardiogram (ECG) signal for an occupant of the environment;
   an environmental sensor configured to sense environmental data selected from a group consisting of the environmental temperature, an ambient temperature, air velocity, sun load and humidity; and
   a heart rate variability (HRV) controller configured to:
      receive the ECG signal;
      identify inter-beat intervals based on the ECG signal; and
      control the HVAC system based on the inter-beat intervals and the environmental data, wherein the HRV controller is further configured to:
      compare the inter-beat intervals to a first threshold and a second threshold, wherein the first threshold is less than the second threshold;
      increase heating in the environment when at least one of the inter-beat intervals is less than the first threshold; and
      increase cooling in the environment when at least one of the inter-beat intervals is greater than the second threshold.

2. The temperature control system of claim 1, wherein the HRV controller is further configured to:
   adjust at least one of the first threshold and the second threshold in response to a manual setpoint change to the HVAC system; and
   use the adjusted value of the at least one of the first threshold and the second threshold to control the HVAC system.

3. The temperature control system of claim 1, wherein the HRV controller is configured to control the HVAC system further based on variations in the inter-beat intervals.

4. A temperature control system, comprising:
   a heating, ventilation and air conditioning (HVAC) system configured to control temperature in an environment;
   a sensor configured to generate an electrocardiogram (ECG) signal for an occupant of the environment;
   an environmental sensor configured to sense environmental data selected from a group consisting of the environmental temperature, an ambient termerature, air velocity, sun load and humidity; and
   a heart rate variability (HRV) controller configured to:
      receive the ECG signal;
      identify inter-beat intervals based on the ECG signal; and
      control the HVAC system based on the inter-beat intervals and the environmental data, wherein the HRV controller is further configured to:
      compare a variation in the inter-beat intervals to a predetermined variation threshold;
      control the HVAC system using a temperature setpoint when the variation is greater than the predetermined variation threshold; and
      control the HVAC system using a correlation between the inter-beat intervals and comfort of the occupant of the environment when the variation is less than the predetermined variation threshold.

5. A temperature control system, comprising:
   a heating, ventilation and air conditioning (HVAC) system configured to control temperature in an environment;
   a sensor configured to generate an electrocardiogram (ECG) signal for an occupant of the environment;
   an environmental sensor configured to sense environmental data selected from a group consisting of the environmental temperature, an ambient temperature, air velocity, sun load and humidity; and
   a heart rate variability (HRV) controller configured to:
      receive the ECG signal;
      identify inter-beat intervals based on the ECG signal; and
      control the HVAC system based on the inter-beat intervals and the environmental data, wherein the HRV controller is further configured to:
      generate N HRV parameters based on the inter-beat intervals, where N is an integer greater than one; and
      use a comfort classification model defined in a N-dimensional HRV parameter space.

6. The temperature control system of claim 5, wherein the HRV controller is further configured to determine the comfort of the occupant of the environment based on the N HRV parameters and the comfort classification model.

7. The temperature control system of claim 5, wherein the comfort classification model defines at least one comfort region in the N-dimensional HRV parameter space and at least one discomfort region in the N-dimensional HRV parameter space.

8. The temperature control system of claim 5, wherein the HRV controller is further configured to train the comfort classification model based on manual setpoint changes to the HVAC system.

9. A vehicle comprising:
   the temperature control system of claim 5;
   a telematics system; and
   wherein the HRV controller is further configured to:
      transmit data relating to the N HRV parameters, the environmental data and manual setpoint changes to the HVAC system via the telematics system to a remote classification training system; and
      receive an updated comfort classification model via the telematics system from the remote classification training system.

10. The temperature control system of claim 5, wherein the HRV controller is further configured to, in response to a manual setpoint change to the HVAC system, retrain the comfort classification model based on the manual setpoint change.

11. The temperature control system of claim 5, wherein the HRV controller is further configured to control the HVAC system based on the inter-beat intervals, the environmental data, and the N HRV parameters.

12. A method for controlling temperature in an environment, comprising:
   controlling the temperature in the environment using a heating, ventilation and air conditioning (HVAC) system;
   generating an electrocardiogram (ECG) signal for an occupant of the environment;
   generating environmental data selected from a group consisting of the environmental temperature, an ambient temperature, humidity, sun load and air velocity;
   identifying inter-beat intervals based on the ECG signal;
   controlling the HVAC system based on the inter-beat intervals and the environmental data;
   comparing the inter-beat intervals to a first threshold and a second threshold, wherein the first threshold is less than the second threshold;
   increasing heating in the environment when at least one of the inter-beat intervals is less than the first threshold; and
   increasing cooling in the environment when at least one of the inter-beat intervals is greater than the second threshold.

13. The method of claim 12, further comprising controlling the HVAC system further based on variations in the inter-beat intervals.

14. The method of claim 12 further comprising:
   adjusting at least one of the first threshold and the second threshold in response to a manual setpoint change to the HVAC system; and
   using the adjusted value of the at least one of the first threshold and the second threshold to control the HVAC system.

15. A method for controlling temperature in an environment, comprising:
   controlling the temperature in the environment using a heating, ventilation and air conditioning (HVAC) system;
   generating an electrocardiogram (ECG) signal for an occupant of the environment;
   generating environmental data selected from a group consisting of the environmental temperature, an ambient temperature, humidity, sun load and air velocity;
   identifying inter-beat intervals based on the ECG signal;
   controlling the HVAC system based on the inter-beat intervals and the environmental data;
   comparing a variation in the inter-beat intervals to a predetermined variation threshold;
   controlling the HVAC system using a temperature setpoint when the variation is greater than the predetermined variation threshold; and
   controlling the HVAC system using a correlation between the inter-beat intervals and comfort of the occupant when the variation is less than the predetermined variation threshold.

16. A method for controlling temperature in an environment, comprising:
   controlling the temperature in the environment using a heating, ventilation and air conditioning (HVAC) system;
   generating an electrocardiogram (ECG) signal for an occupant of the environment;
   generating environmental data selected from a group consisting of the environmental temperature, an ambient temperature, humidity, sun load and air velocity;
   identifying inter-beat intervals based on the ECG signal;
   controlling the HVAC system based on the inter-beat intervals and the environmental data;
   generating N heart rate variability (HRV) parameters based on the inter-beat intervals, where N is an integer greater than one; and
   using a comfort classification model defined in a N-dimensional HRV parameter space.

17. The method of claim 16, further comprising determining comfort of the occupant based on the N HRV parameters and the comfort classification model.

18. The method of claim 17, wherein the comfort classification model defines at least one comfort region in the N-dimensional HRV parameter space and at least one discomfort region in the N-dimensional HRV parameter space.

19. The method of claim 17, further comprising training the comfort classification model in response to manual setpoint changes to the HVAC system.

20. The method of claim 17, further comprising:
   transmitting data relating to the N HRV parameters, the environmental data, and manual setpoint changes to the HVAC system via a telematics system to a remote classification training system; and
   receiving an updated comfort classification model via the telematics system from the remote classification training system.

21. The method of claim 17, further comprising, in response to manual setpoint changes to the HVAC system, retraining the comfort classification model.

22. The method of claim 16, further comprising controlling the HVAC system based on the inter-beat intervals, the environmental data, and the N HRV parameter.

* * * * *